(12) United States Patent
Sasaki

(10) Patent No.: US 6,238,380 B1
(45) Date of Patent: May 29, 2001

(54) DISPOSABLE DIAPER

(75) Inventor: Toru Sasaki, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/295,152

(22) Filed: Apr. 20, 1999

(30) Foreign Application Priority Data

Apr. 20, 1998 (JP) .................................................. 10-109960

(51) Int. Cl.$^7$ ...................................................... A61F 13/15
(52) U.S. Cl. ............... 604/385.01; 604/358; 604/385.29; 604/385.101
(58) Field of Search ............... 604/358, 385.01, 604/385.24, 385.101

(56) References Cited

U.S. PATENT DOCUMENTS 4,822,435 * 4/1989 Igaue et al. ........................... 156/164
5,458,592   10/1995 Abuto et al. .
5,520,673    5/1996 Yarborough et al. .

FOREIGN PATENT DOCUMENTS 0593082   4/1994 (EP) .
0781539   7/1997 (EP) .
52-40267 * 10/1977 (JP) .

* cited by examiner

*Primary Examiner*—John G. Weiss
*Assistant Examiner*—Paul Shanoski
(74) *Attorney, Agent, or Firm*—Baker & Daniels

(57) ABSTRACT

In a disposable diaper, a topsheet covering a top surface of a liquid-absorbent core is folded along side edges of the core so as to cover a bottom surface of the core. On the bottom surface of the core, the topsheet is bonded to a backsheet along zones respectively spaced from side edges of the core towards a center line of the diaper. Elastic members provided in association with leg-openings are secured to the backsheet in vicinity of the respective side edges of the core.

4 Claims, 3 Drawing Sheets

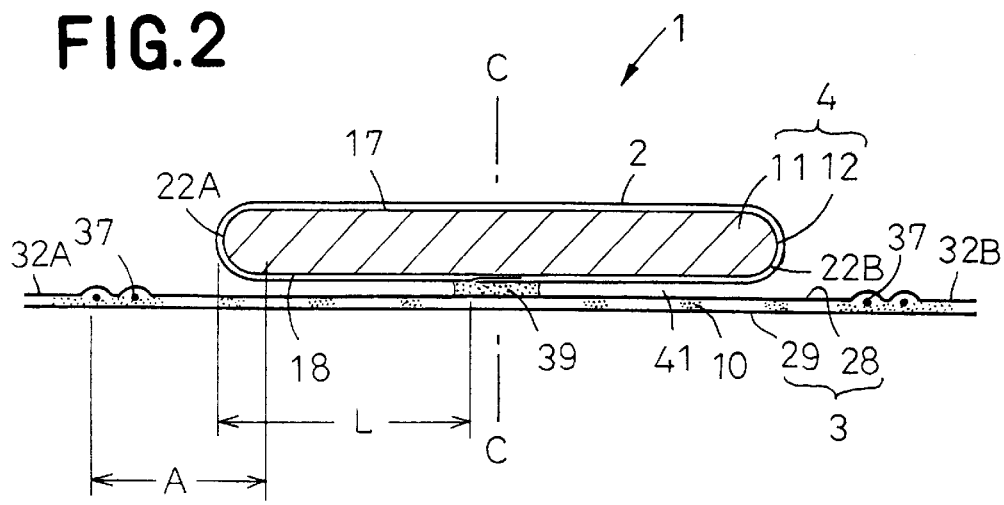
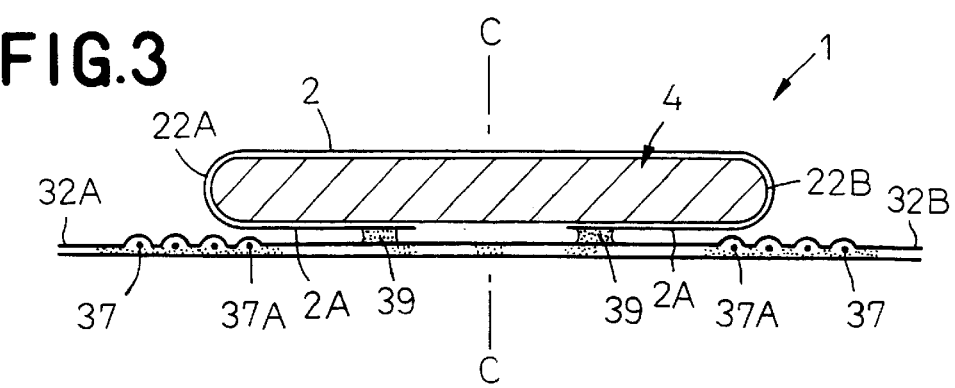
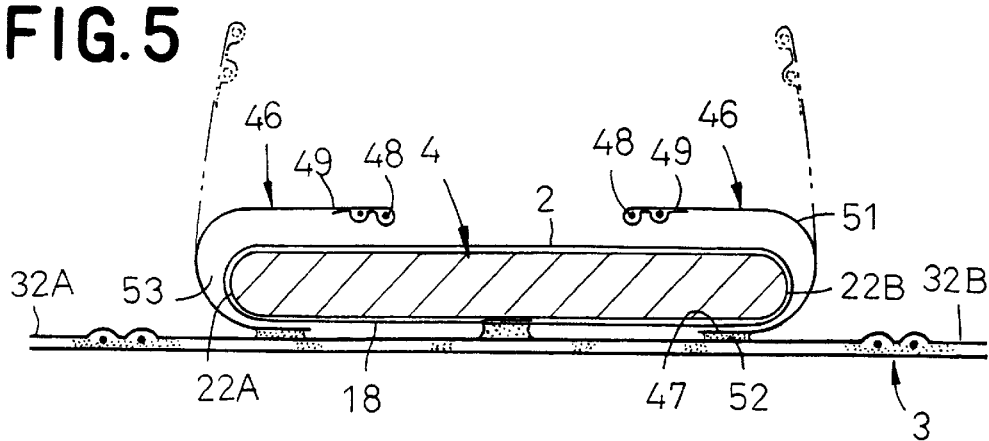

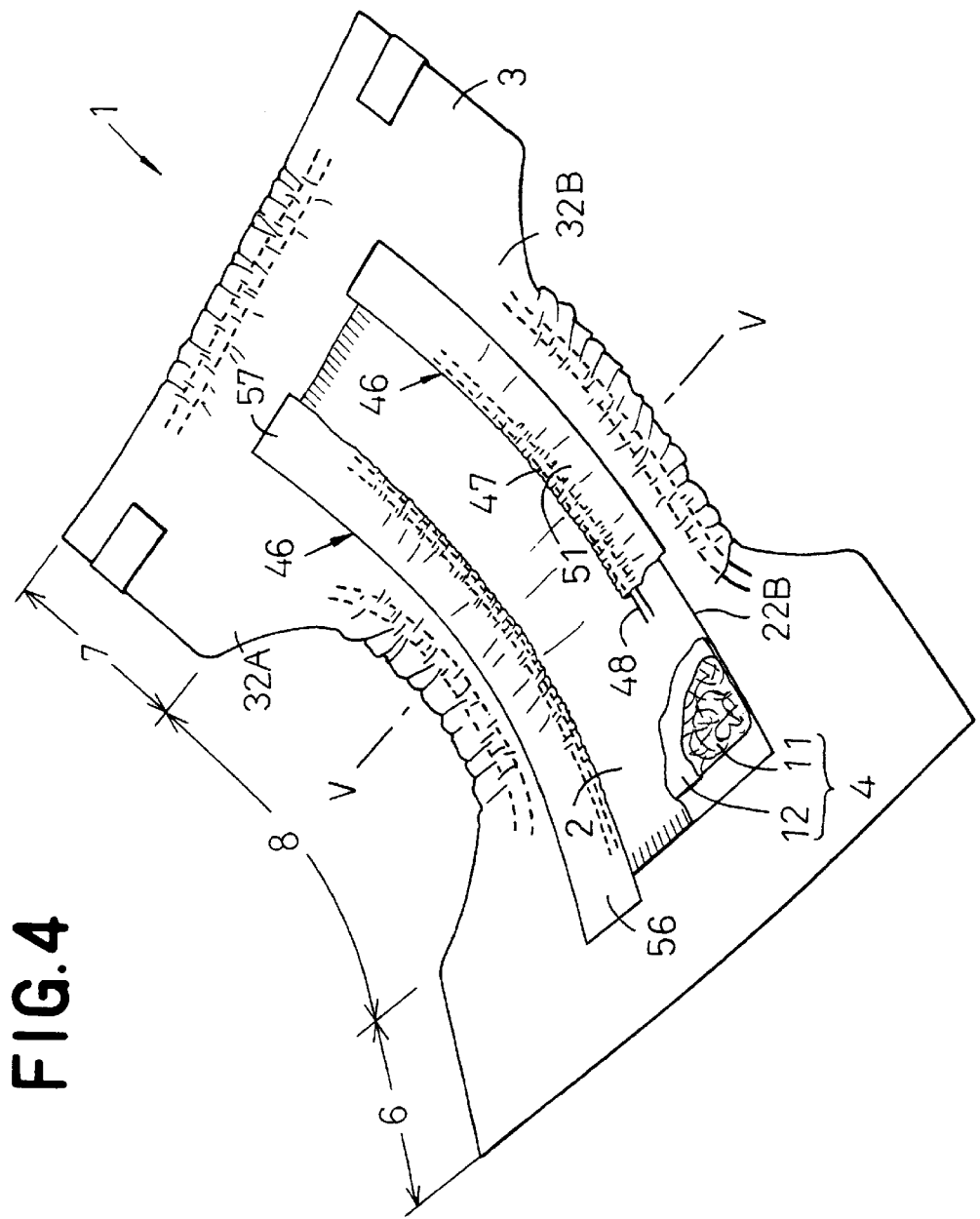

DISPOSABLE DIAPER

BACKGROUND OF THE INVENTION

This invention relates to disposable diapers for absorbing and containing body exudates.

Japanese Patent Publication No. Sho52-40267 discloses a disposable diaper comprising a liquid-pervious topsheet, a liquid-impervious backsheet and a liquid-absorbent core disposed between these two sheets. The topsheet and the backsheet are bonded together along their portions extending outwards beyond a peripheral edge of the core. The known diaper is provided in proximity of its transversely opposite side edges with elastic members extending longitudinally of the diaper so that the lines along which these elastic members are stretched and contracted should be spaced from respective side edges of the core at least by 1.91 cm.

According to the disclosure of the Japanese Patent Publication No. Sho52-40267, the elastic members provided in association with leg-openings are spaced from the respective side edges of the core by 1.91 cm or more so that these elastic members may be free from a restriction by the core of a relatively high rigidity. According to such disclosure, it will be desired to further enlarge the distance by which the elastic members should be spaced from the respective side edges of the core as a rigidity of the core increases. However, a width of the crotch region of the diaper may be unacceptably enlarged as the distance is enlarged.

SUMMARY OF THE INVENTION

In view of the problem as has been described above, it is an object of the present invention to provide a disposable diaper allowing the elastic members associated with the leg-openings to be stretchable and contractile freely from any restriction by the rigidity of the core.

According to one embodiment of the invention, there is provided a disposable diaper comprising a liquid-pervious topsheet, a liquid-impervious backsheet and a liquid-absorbent core disposed between the topsheet and the backsheet which define a front waist region, a rear waist region and a crotch region extending between the front waist region and the rear waist region, and elastic members associated with leg-openings longitudinally extending along transversely opposite side edges of the diaper from the crotch region into the front and rear waist regions, wherein:

the core extends across the crotch region into the front and rear waist regions and has a top surface facing a body side of a wearer, a bottom surface opposed to the top surface, longitudinally opposite ends extending circumferentially of the diaper and transversely opposite side edges extending longitudinally of the diaper; the topsheet covering the top surface of the core is folded along the side edges of the core onto the bottom surface of the core so as to cover the bottom surface at least partially; the backsheet underlies the sections of the topsheet folded onto the bottom surface of the core and extends outwards beyond the side edges of the core; the sections of the topsheet folded onto the bottom surface of the core are bonded to the backsheet along zones extending, inside the side edges of the core, in parallel to a center line dividing a width of the diaper in two halves; and the elastic members associated with the leg-openings are secured to the backsheet in vicinity of the side edges of the core.

According to one embodiment of the present invention, the elastic members associated with the leg-openings respectively lie in the crotch region of the diaper within a range corresponding to a width defined by 10 mm as measured inwardly from the side edges of the core plus 30 mm as measured outwardly from the lateral surfaces.

According to another embodiment of the present invention, the backsheet is formed on its inner surface with a pair of barrier cuffs each having a relatively deformable distal edge extending longitudinally of the diaper inside each of the side edges of the core, a proximal edge fixed to the inner surface of the backsheet outside or inside the side edge of the core and extending in parallel to the distal edge, and an elastic member secured to the distal edge along an apex thereof under tension given longitudinally of the diaper so that the barrier cuff is normally biased by the tension to rise on the inner surface of the backsheet.

BRIEF DESCRIPTION OF THE DRAWINGS

FIG. 2 is a sectional view taken along line II—II in FIG. 1;

FIG. 3 is a view similar to FIG. 2 showing another embodiment of the present invention;

FIG. 4 is a view similar to FIG. 2 showing still another embodiment of the present invention; and FIG. 5 is a sectional view taken along line V—V in FIG. 4.

DETAILED DESCRIPTION OF THE PREFERRED EMBODIMENTS

Figure 1:
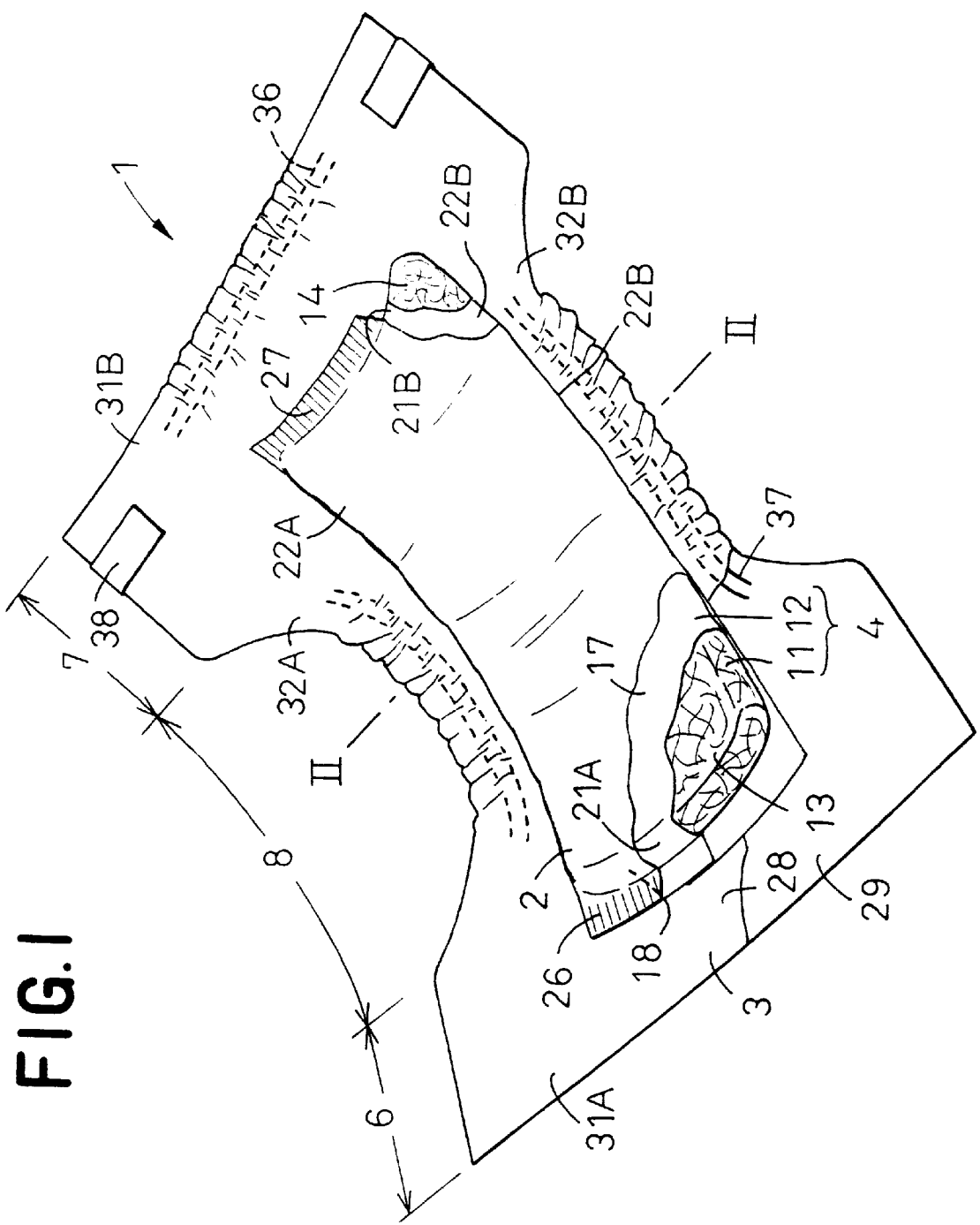
FIG. 1 is a perspective view showing a disposable diaper according to the present invention as partially broken away.

Details of a disposable diaper according to the present invention will be more fully understood from the description given hereunder with reference to the accompanying drawings.

Diaper 1 shown by FIG. 1 in a perspective view as partially broken away comprises a liquid-pervious topsheet 2, a liquid-absorbent core 4 covered with the topsheet 2 and an hourglass-shaped liquid-impervious backsheet 3. The diaper 1 has a front waist region 6, a rear waist region 7 and a crotch region 8 extending between the front and rear waist regions 6, 7.

The core 4 is formed by a liquid-absorbent material 11 comprising a mixture of fluff pulp and superabsorptive polymer particles. The liquid-absorbent material 11 is covered with a tissue paper 12 and extends across the crotch region 8 into the front and rear waist regions 6, 7. The core 4 is substantially rectangular or hourglass-shaped and defined by a top surface 17 facing a body side of a wear, a bottom surface 18 opposed to the top surface 17 (See FIG. 2), longitudinally opposite ends 21A, 21B extending circumferentially of the diaper 1, and transversely opposite side edges 22A, 22B extending longitudinally of the diaper 1.

The topsheet 2 covers the top surface 17 of the core 4 and is folded along the side edges 22A, 22B onto the bottom surface 18 so as to extend inwards transversely of the core 4 until transversely opposite side edges of the topsheet 2 thus folded overlap each other in proximity of a center line C—C of the core 4 (See FIG. 2). Both sections of the topsheet 2 covering the top and bottom surfaces 17, 18 of the core 4, respectively, longitudinally extend beyond the longitudinally opposite ends 21A, 21B of the core 4 so as to be placed upon and bonded to each other along their respective extensions.

The backsheet 3 is provided in the form of a laminate sheet which comprises an inner layer sheet 28 made of a liquid-impervious plastic film and an outer layer sheet 29 made of a nonwoven fabric bonded to the inner layer sheet 28 by means of adhesive 10 (See FIG. 1). The backsheet 3 underlies the sections of the topsheet 2 folded onto the bottom surface of the core 4. The backsheet 3 extends outwards beyond the longitudinally opposite ends 21A, 21B as well as beyond the transversely opposite side edges 22A, 22B of the core 4 to form longitudinally opposite ends 31A, 31B extending circumferentially of the diaper 1 and transversely opposite side edges 32A, 32B extending longitudinally of the diaper 1. The rear end 31B and the side edges 32A, 32B are provided with elastic members 36 associated with a waist-opening and elastic members 37, 37 associated with a pair of leg-openings, respectively. These elastic members 36, 37, 37 are disposed between the inner and outer layer sheets 28, 29 and secured to an inner surface of at least one of the inner and outer layer sheets 28, 29. A pair of tape fasteners 38, 38 are attached to the backsheet 3 in proximity of its respective side edges 32A, 32B of the rear waist region 7.

FIG. 2 is a sectional view taken along line II—II in FIG. 1. The bottom surface 18 of the core 4 covered with the topsheet 2 is bonded in its central zone to the backsheet 3 by means of adhesive 39, leaving the remaining zones extending in vicinity of its side edges 22A, 22B free so that a gap 41 may be formed between the bottom surface 18 and the backsheet 3. Longitudinally of the diaper 1, a zone applied with the adhesive 39 extends continuously or intermittently to the front and rear ends 21A, 21B of the core 4, or to points in vicinity thereof. Transversely of the crotch region 8, a zone applied with the adhesive 39 is spaced from each of the side edges 22A, 22B of the core 4 by a distance L which is preferably 15 mm or longer, more preferably 20 mm or longer. Transversely of the crotch region 8 again, the elastic member 37 associated with each leg-opening lies within a range corresponding to a width defined by 10 mm as measured inwardly from each of the side edge 22A, 22B of the core 4 towards the center line C—C of the diaper 1 30 mm as measured outwardly from each of the side edge 22A, 22B. In proximity of the front and rear ends 21A, 21B of the core 4, it is also possible to bond the core 4 over its full width to the backsheet 3 with the topsheet 2 disposed therebetween.

The diaper 1 of such an arrangement allows the elastic members 37, 37 associated with the pair of leg-openings to be stretchable and contractile freely from any restriction by a rigidity of the core 4. Accordingly, the elastic members 37, 37 associated with the pair of leg-openings may be placed adjacent the core 4 to prevent excretion from leaking sideways even if the core 4 is of a relatively high rigidity. This allows, in turn, a width of the crotch region 8 to be sufficiently restricted to obtain a good feeling to wear the diaper 1. With this diaper 1, on the other hand, body fluids can be absorbed by the core 4 through its bottom surface also and therefore the effective surface area of the core 4 for direct absorption of body fluids is substantially larger than the conventional diaper adapted to absorb most of body fluids by the core through its top surface and side edges. In this way, an absorption rate of the core can be correspondingly improved.

FIG. 3 is a view similar to FIG. 2 showing another embodiment of the present invention. In the case of this diaper 1, the side sections 2A, 2A of the topsheet 2 folded onto the bottom surface of the core 4 are bonded by means of the adhesive 39 to the backsheet 3 without being overlapped each other. The elastic members 37 associated with the leg-openings lie inside as well as outside the respective side edges 22A, 22B of the core 4. The elastic members 37A lying inside the respective side edges 22A, 22B function to press the core 4 against the wearer's skin.

FIG. 4 is a view similar to FIG. 1 showing another embodiment of the present invention and FIG. 5 is a sectional view taken along line V—V in FIG. 4. This diaper 1 is provided along the transversely opposite side edges 32, 32 with a pair of barrier cuffs 46, 46 extending from the crotch region 8 into the front and rear waist regions 6, 7. Each of the barrier cuffs 46 is made of a nonwoven fabric, preferably of a substantially liquid-impervious nonwoven fabric, more preferably of a breathable but liquid-impervious nonwoven fabric. The barrier cuffs 46 are bonded to the inner surface of the backsheet 3 by means of adhesive 52 and has a proximal edge 47 extending longitudinally of the diaper 1, a distal edge 49 extending in parallel to the proximal edge 47 and provided with an elastic member 48 bonded to the distal edge 49 under longitudinal tension, and an intermediate region 51 extending between these two edges 47, 49. The proximal edge 47 may be bonded to the backsheet 3 along a zone lying inside or outside, preferably inside each of the side edge 22A, 22B of the core 4. In the case of the embodiment shown in FIG. 5, the proximal edge 47 lies inside the side edge 23 of the core 4 so that a pocket 53 is formed between the barrier cuff 46 and the bottom surface 18 of the core 4. During storage of the diaper 1, front and rear ends 56, 57 of the barrier cuffs 46 are collapsed outwardly or inwardly of the diaper 1 and, in their collapsed states, bonded to the topsheet 2 and/or the backsheet 3. FIG. 4 shows the case in which these front and rear ends 56, 57 of the barrier cuffs 46 are collapsed inwardly of the diaper 1. When put on the wearer's body, the diaper 1 is longitudinally curved with the core 4 inside and the elastic members 48 contracted. Thereupon, the barrier cuffs 46 rise on an inner surface of the diaper 1 as indicated by imaginary lines in FIG. 5. While body fluids discharged on the diaper 1 partially flow sideways, they are prevented by the barrier cuffs 46 from further flowing sideways. Body fluids thus obstructed by the barrier cuffs 46 are forced to flow along the barrier cuffs 46 towards the bottom surface 18 of the core 4 and are absorbed by the core 4 first through the section of the topsheet 2 covering the bottom surface 18 of the core 4 and then through the bottom surface 18. The present embodiment of the diaper 1 enables body fluids to flow towards the bottom surface 18 of the core 4 more reliably than with the embodiment shown in FIG. 1.

To exploit the present invention, the topsheet 2 may be made of a nonwoven fabric or an apertured plastic film. The respective members of the diaper 1 may be bonded together using a suitable adhesive agent such as hot melt adhesive. For the members of hot melt type, the heat-sealing technique may be utilized.

With the disposable diaper according to the present invention, the elastic members secured to the backsheet in association with the leg-openings are stretchable as well as contractile freely from any restriction by the liquid-absorbent core, since the side edges of the core are spaced from the backsheet. Accordingly, the width of the crotch region can be limited as desired as possible, since the elastic members associated with the leg-openings can be placed adjacent the side edges of the core even if the core is of a relatively high rigidity.

Furthermore, the present invention enables body fluids discharged on the diaper to be partially absorbed through the bottom surface of the core so that not only an absorption rate of the core can be improved but also an amount of body fluids collected in vicinity of the core can be rapidly absorbed by the core to avoid a sideways leakage of body fluids.

What is claimed is:

1. A disposable diaper comprising:

liquid-pervious topsheet:

a liquid-impervious backsheet; and a liquid-absorbent core disposed between said topsheet and said backsheet, said liquid-pervious topsheet, liquid-impervious backsheet and liquid-absorbent core defining a front waist region, a rear waist region and a crotch region extending between said front waist region and said rear waist region, said disposable diaper further comprising elastic members longitudinally extending along transversely opposite side edges of said diaper from said crotch region into said front and rear waist regions, said liquid-absorbent core extending across said crotch region into said front and rear waist regions and having a top surface for facing a wearer, a bottom surface opposed to said top surface, longitudinally opposite ends and transversely opposite side edges, said liquid-pervious topsheet covering said top surface of said liquid-absorbent core and being folded along said opposed side edges of said liquid-absorbent core and extending onto said bottom surface of said liquid-absorbent core so as to cover said bottom surface at least partially, said liquid-impervious backsheet underlying portions of said liquid-pervious topsheet which are folded onto said bottom surface of said liquid-absorbent core and extending outwards beyond said opposite side edges of said liquid-absorbent core, said portions of said liquid-pervious topsheet which are folded onto said bottom surface of said liquid-absorbent core being bonded to said liquid-impervious backsheet along zones which extend inside said opposite side edges of said liquid-absorbent core, parallel to a center line which divides a width of the diaper in two halves, and said elastic members being bonded to said liquid-impervious backsheet in proximity to said opposite side edges of said liquid-absorbent core.

2. A disposable diaper according to claim 1, wherein said elastic members are positioned in said crotch region of the diaper within a range defined between a point measured 10 mm inwardly from said opposite side edges of said liquid-absorbent core and another point measured 30 mm outwardly from said opposite side edges.

3. A disposable diaper according to claim 1, wherein said liquid-impervious backsheet is formed on an inner surface thereof with a pair of barrier cuffs, each of said barrier cuffs having:

a deformable distal edge which extends longitudinally of said diaper inside each of said opposite side edges of said liquid-absorbent core;

a proximal edge fixed to said inner surface of said liquid-impervious backsheet outside said opposite side edge of said liquid-absorbent core and extending in parallel to said distal edge and an elastic member secured to said distal edge along an apex thereof under tension so that said barrier cuffs are normally biased by said tension to rise on said inner surface of said liquid-impervious backsheet.

4. A disposable diaper according to claim 1, wherein said liquid-impervious backsheet is formed on an inner surface thereof with a pair of barrier cuffs, each of said barrier cuffs having:

a deformable distal edge which extends longitudinally of said diaper inside each of said opposite side edges of said liquid-absorbent core;

a proximal edge fixed to said inner surface of said liquid-impervious backsheet inside said opposite side edge of said liquid-absorbent core and extending in parallel to said distal edge and an elastic member secured to said distal edge along an apex thereof under tension so that said barrier cuffs are normally biased by said tension to rise on said inner surface of said liquid-impervious backsheet.

* * * * *